US012678169B2

(12) United States Patent
Ellis

(10) Patent No.: US 12,678,169 B2
(45) Date of Patent: Jul. 14, 2026

(54) PRESSURE LIMITED TRAINING TOURNIQUET

(71) Applicant: SIMETRI, Inc., Winter Park, FL (US)

(72) Inventor: Trevor Ellis, Longwood, FL (US)

(73) Assignee: SIMETRI, INC., Winter Park, FL (US)

( * ) Notice: Subject to any disclaimer, the term of this patent is extended or adjusted under 35 U.S.C. 154(b) by 470 days.

(21) Appl. No.: 18/373,622

(22) Filed: Sep. 27, 2023

(65) Prior Publication Data

US 2024/0108357 A1     Apr. 4, 2024

Related U.S. Application Data

(60) Provisional application No. 63/411,349, filed on Sep. 29, 2022.

(51) Int. Cl.
*A61B 17/132*     (2006.01)
*G09B 23/28*     (2006.01)

(52) U.S. Cl.
CPC .......... *A61B 17/1322* (2013.01); *G09B 23/28* (2013.01)

(58) Field of Classification Search
CPC ............................ A61B 17/1322; G09B 23/28
USPC ........................................... 434/262; 600/587
See application file for complete search history.

(56) References Cited

U.S. PATENT DOCUMENTS

| | | | | |
|---|---|---|---|---|
| 8,047,850 | B2 * | 11/2011 | Esposito ................ | G09B 23/28 |
| | | | | 434/262 |
| 2009/0005804 | A1 | 1/2009 | Esposito et al. | |
| 2010/0234877 | A1 * | 9/2010 | Pienkowski ....... | A61B 17/1325 |
| | | | | 606/203 |
| 2020/0005675 | A1 * | 1/2020 | Quail ..................... | G09B 23/28 |
| 2022/0047273 | A1 | 2/2022 | Parsons et al. | |

FOREIGN PATENT DOCUMENTS

WO     2021041006 A2     3/2021

OTHER PUBLICATIONS

European Search Report, Appl. No. EP23200038, Feb. 15, 2024.

* cited by examiner

*Primary Examiner* — Dmitry Suhol
*Assistant Examiner* — Alyssa N Brandley
(74) *Attorney, Agent, or Firm* — Joseph R. Englander, Esq.; Lewis Brisbois Bisgaard & Smith LLP

(57) ABSTRACT

A pressure limited training tourniquet includes a platform. A first strap, affixed to the platform, affixes the platform to an appendage of a person. A first support is slidably disposed on the platform. A second support is slidably disposed on the platform. A spring has a first end and a second end. The spring first end is affixed to the first support and spring second end is affixed to the second support. A second strap is affixed to the first support and the second support. A windlass is operatively coupled to the second strap, such that rotation of the windlass causes the first support and second support to move away from each other, causing the spring to expand. A sensor disposed between the sensor cover and the platform measures a compression force applied by way of the sensor cover to the platform.

10 Claims, 1 Drawing Sheet

PRESSURE LIMITED TRAINING TOURNIQUET

CROSS REFERENCE TO RELATED APPLICATION

This application claims the benefit of U.S. Provisional Patent Application No. 63/411,349 filed Sep. 29, 2022, the contents of which are herein incorporated.

BACKGROUND OF THE INVENTION

The present invention is directed to a tourniquet for controlling blood flow to a wound and more particularly to a training tourniquet for use in training tourniquet technique which prevents exertion of too much pressure to the limb of a subject about which the tourniquet is placed.

Medical personnel, whether nurses in a hospital, emergency medical technicians, medics in the field, and even police and fire personnel need training in attending to wounds. One technique that requires training is the staunching of bleeding. One common technique for staunching bleeding is the use of a tourniquet about a limb above the wound.

The proper use of a tourniquet requires training including the repetitive performance of the technique. While it is known to practice on a mannequin, it is best to practice tourniquet techniques on an actual person. However, until the practitioner perfects their technique, such practice often results in over tightening of the tourniquet. This causes pain and even bruising to the person upon whom the technique is being performed.

Accordingly, a system which overcomes the shortcomings of the prior art is desired.

SUMMARY OF THE INVENTION

A pressure limited training tourniquet includes a platform. A first strap adapted to affix the platform to an appendage of a person is affixed to the platform. A first support is slidably disposed on the platform. A second support is slidably disposed on the platform. A spring has a first end and a second end. The first end of the spring is affixed to the first support and the second end of the spring is affixed to the second support. A second strap is affixed to the first support and the second support. A windlass is operatively coupled to the second strap, such that rotation of the windlass causes the first support and second support to move in a direction away from each other, causing the at least one spring to expand. A sensor disposed between a sensor cover and the platform measures a compression force applied by the second strap to the sensor.

In a further embodiment of the invention the sensor cover, to protect the sensor, is disposed between the sensor and the second strap. The pressure applied to the sensor cover is applied in turn to the sensor.

BRIEF DESCRIPTION OF THE DRAWINGS

The features and advantages of the present invention will become more readily apparent from the following detailed description of the invention in which like elements are labeled similarly and in which.

DETAILED DESCRIPTION OF THE PREFERRED EMBODIMENTS

Figures 1, 1A, 2, 2A:
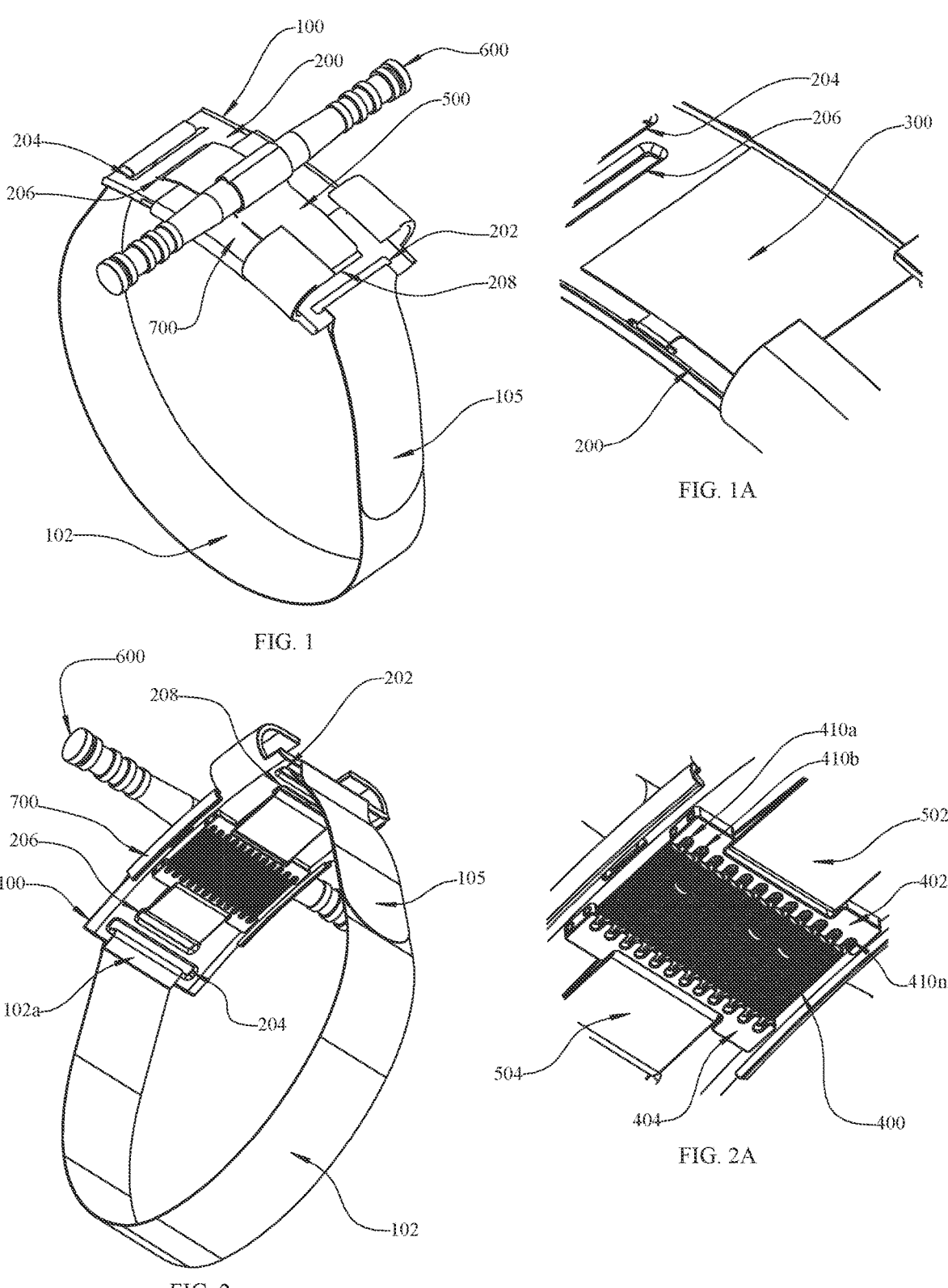
FIG. 1 is a top perspective view of a tourniquet constructed in accordance with the invention.
FIG. 1A is a top perspective view of a sensor disposed on the tourniquet constructed in accordance with the invention.
FIG. 2 is a bottom perspective view of the tourniquet constructed in accordance with the invention.
FIG. 2A is a bottom perspective view of the tourniquet constructed in accordance with the invention.

Reference is now made to FIGS. 1 and 2 in which a pressure limited training tourniquet, generally indicated as 100 is shown. Tourniquet 100 includes a platform 200 having receiving slots 202, 204 for receiving ends 102a, 105 of a strap 102 therethrough. In this way, platform 200 and strap 102 encircle a limb of a person being treated. As known in the art, end 102a is fixedly secured to platform 200 at receiving slot 204 and end 105 secures upon itself using Velcro® fastener or some other fastening means at receiving slot 202 to adjust the length of strap 102 to snugly fit each person being treated.

A first support 402 is slidably disposed on a limb facing surface of platform 200. A second support 404 is slidably disposed on a limb facing surface of platform 200 spaced from first support 402. At least one spring, and preferably a plurality of springs 410a-410n, are supported at first end thereof by support 402 and at a second end thereof by support 404. In this way, springs 410a-410n apply a force biasing supports 402, 404 towards each other and when either or both of supports 402, 404 are moved away from each other, springs 410a-410n are stretched, they become elongated.

Platform 200 is formed with a third receiving slot 206 therein and a fourth receiving slot 208 therein. A second strap 500 extends through third receiving slot 206 and a fourth receiving slot 208. Strap 500 is affixed to first support 402 at a first end 502 of second strap 500 and affixed to second support 404 at a second end 504 of second strap 500. A windlass 600 is operatively coupled to strap 500 to tighten strap 500 relative to platform 200.

A sensor 300 for measuring a force applied thereto is disposed on a surface of platform 200 facing away from the limb (see FIG. 1A) between platform 200 and a sensor cover 700. As windlass 600 tightens strap 500, strap 500 exerts a force in the direction of sensor 300 measured as a pressure about the limb. Sensor cover 700 is disposed between strap 500 and sensor 300 to protect sensor 300, but is sufficiently pliable to transmit the force applied to cover 700 to sensor 300.

At the same time, as windlass 600 tightens strap 500, strap 500 exerts a force at ends 502, 504 of strap 500. Strap 500 is in effect pulled towards pressure sensor 300. Once the force exceeds a predetermined amount, determined by the strength of springs 410a-410n, ends 502, 504 coupled to respective supports 402, 404 pull supports 402, 404 apart, stretching springs 410a-410n. Sensor 300 experience the force, but the limb of the test subject does not. The force is "transferred" from strap 102, where it would normally be expressed to the limb of the person being treated, to springs 410 which absorb the force in a way not felt by the person being treated, but capable of enabling the trainee to obtain feedback regarding tightening techniques. In this way, the tightening is not felt by the person being treated, no bruising or pain occurs.

The sensor 300 is connected to a display either visual or audible, not shown, which provides feedback to the user when the trainee has applied the appropriate number of turns to windlass 600. In other words, when pain would have been experienced by the person to whom the tourniquet is applied, or similarly, when sufficient pressure would have been applied to staunch bleeding.

It will thus be seen that the objects set forth above, among those made apparent from the preceding description, are efficiently attained and, since certain changes may be made in carrying out the above method and in the construction set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

What is claimed is:

1. A pressure limited training tourniquet comprises:
a platform;
a first strap affixed to the platform, the first strap being adapted to affix the platform to an appendage of a person to be treated;
a first support slidably disposed on the platform;
a second support slidably disposed on the platform;
at least one spring having a first end and a second end; the first end of the at least one spring being affixed to the first support and the second end of the at least one spring being affixed to the second support;
a second strap affixed to the first support and the second support;
a windlass operatively coupled to the second strap; such that rotation of the windlass causing the first support and the second support to move away from each other; causing the at least one spring to expand; and a sensor disposed between the second strap and the platform measuring a compression force applied by the second strap to the sensor.

2. The pressure limited training tourniquet of claim 1, further comprising a cover disposed between the second strap and the sensor, the cover transmitting a force from the second strap to the sensor.

3. The pressure limited training tourniquet of claim 1, wherein the platform further comprises:
at least one receiving slot for receiving at least a first end of at least the first strap.

4. The pressure limited training tourniquet of claim 1, further comprising a fastening means for affixing the first strap to the platform.

5. The pressure limited training tourniquet of claim 1, wherein the sensor is disposed facing away from the appendage of the person upon which the pressure limited training tourniquet is disposed.

6. The pressure limited training tourniquet of claim 1, wherein the first strap encircles the appendage of the person.

7. The pressure limited training tourniquet of claim 1, wherein at least the first support is disposed on an appendage facing surface of the platform.

8. The pressure limited training tourniquet of claim 1, wherein the sensor operatively communicates with a display, the display providing feedback when the sensor recognizes an appropriate amount of turns have been applied to the windlass.

9. The pressure limited training tourniquet of claim 8, wherein the display is visual.

10. The pressure limited training tourniquet of claim 8, wherein the display is audible.

* * * * *